(12) United States Patent
Eller

(10) Patent No.: US 10,366,784 B1
(45) Date of Patent: Jul. 30, 2019

(54) METHODS AND SYSTEMS FOR PRESCRIPTION TRANSFER

(75) Inventor: Charles E. Eller, Lake Saint Louis, MO (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 0 days.

(21) Appl. No.: 13/299,871

(22) Filed: Nov. 18, 2011

(51) Int. Cl.
G16H 20/10 (2018.01)

(52) U.S. Cl.
CPC .................................. *G16H 20/10* (2018.01)

(58) Field of Classification Search
CPC .............................. G06Q 50/22; G06Q 50/24
USPC .......................................................... 705/2, 3
See application file for complete search history.

(56) References Cited

U.S. PATENT DOCUMENTS

| | | | |
|---|---|---|---|
| 6,202,923 B1* | 3/2001 | Boyer et al. | 235/375 |
| 7,983,995 B2* | 7/2011 | Murphy et al. | 705/332 |
| 8,027,847 B1* | 9/2011 | Francis et al. | 705/2 |
| 8,050,942 B1* | 11/2011 | Ali et al. | 705/2 |
| 8,626,530 B1* | 1/2014 | Tran | G06Q 50/22 705/2 |
| 2002/0035484 A1 | 3/2002 | McCormick | |
| 2003/0179287 A1* | 9/2003 | Kozic et al. | 348/14.08 |
| 2003/0214129 A1* | 11/2003 | Adler | 283/81 |
| 2003/0225595 A1* | 12/2003 | Helmus et al. | 705/2 |
| 2006/0032923 A1* | 2/2006 | Krupa | 235/462.01 |
| 2008/0306761 A1 | 12/2008 | George et al. | |
| 2010/0125461 A1 | 5/2010 | Heald et al. | |
| 2011/0125521 A1* | 5/2011 | Dhoble | 705/2 |
| 2011/0257989 A1* | 10/2011 | Kumar | 705/2 |
| 2014/0142977 A1* | 5/2014 | Chinta | 705/3 |

OTHER PUBLICATIONS

Pharmacist's Manual published on USDOJ website on Dec. 2, 2010.*
Gonzalez et al., Digital Image Processing, 1992, Prentice Hall, Second Edition, Chapter 1 (Year: 1992).*
Liang, J. et al., "Flattening Curved Documents in Images," In Proc. Of the IEEE Conf. On Computer Vision and Pattern Recognition (CVPR), 2005, 8 pages, [online] Retrieved from the Internet. (Year: 2005).*
Roborealm, "Bottle Unwrap", https://web.archive.org/web/20090218134840/http://www.roborealm.com/help/Bottle_Unwrap.php, 2009, 2 pages, [online] Retrieved from the Internet. (Year: 2009).*

(Continued)

*Primary Examiner* — Devin C Hein
(74) *Attorney, Agent, or Firm* — Tucker Arensberg, P.C.

(57) ABSTRACT

Methods and systems for transferring a prescription to a mail order prescription service are described. In one embodiment, an electronic image of a retail pharmacy prescription label is received, in which the image of the retail pharmacy prescription label includes a representation of a retail pharmacy prescription number associated with a prescription drug prescribed to a member. A retail pharmacy associated with the retail pharmacy prescription number is identified. A prescription associated with the retail pharmacy prescription number is identified based on identification of the retail pharmacy. A mail order delivery request to refill the prescription drug for the member at mail order is generated. Other methods and systems are described.

21 Claims, 10 Drawing Sheets

(56) References Cited

OTHER PUBLICATIONS

CVS Pharmacy, http://itunes.apple.com/us/app/cvs-pharmacy/id395545555?mt=8, downloaded on Nov. 18, 2011, Dated Mar. 31, 2011, pp. 1-3.
CVS Caremark, http://www.cvscaremarkfyi.com/blogs/theres-app-cvs-pharmacy, downloaded on Nov. 18, 2011, Dated Mar. 31, 2011, pp. 1-2.

* cited by examiner

800

MESSAGES

TO: 555-555

SMITH PHARMACY
BOSTON, MA

RX 2925713378
JONES, JOHN          DR. M. THOMAS

CARBAMAZEPINE 200MG

REFILLS 1 OF 5
TAKE ONE TABLET BY MOUTH ONCE A DAY AS DIRECTED

METHODS AND SYSTEMS FOR PRESCRIPTION TRANSFER

FIELD

The present disclosure generally relates to the provision of prescription drugs, and more particularly transferring retail prescription drug acquisition.

BACKGROUND

Often when an individual receives a prescription for drugs from a physician, the individual will have the prescription filled at a local retail pharmacy store. The decision to fill the prescription at a retail pharmacy store may often be based upon considerations such as convenience, and a desire or need to begin taking the prescription drug immediately. In the case of an ongoing course of treatment that may include multiple refills of a prescription, convenience and cost savings may be realized through the use of a home delivery pharmacy, which may deliver prescription drugs to the individuals home via a parcel service, such as the US Postal Service, or other parcel service.

BRIEF DESCRIPTION OF THE DRAWINGS

FIGS. 7-9 are example displays, according to example embodiments; and

DETAILED DESCRIPTION

Figure 1:
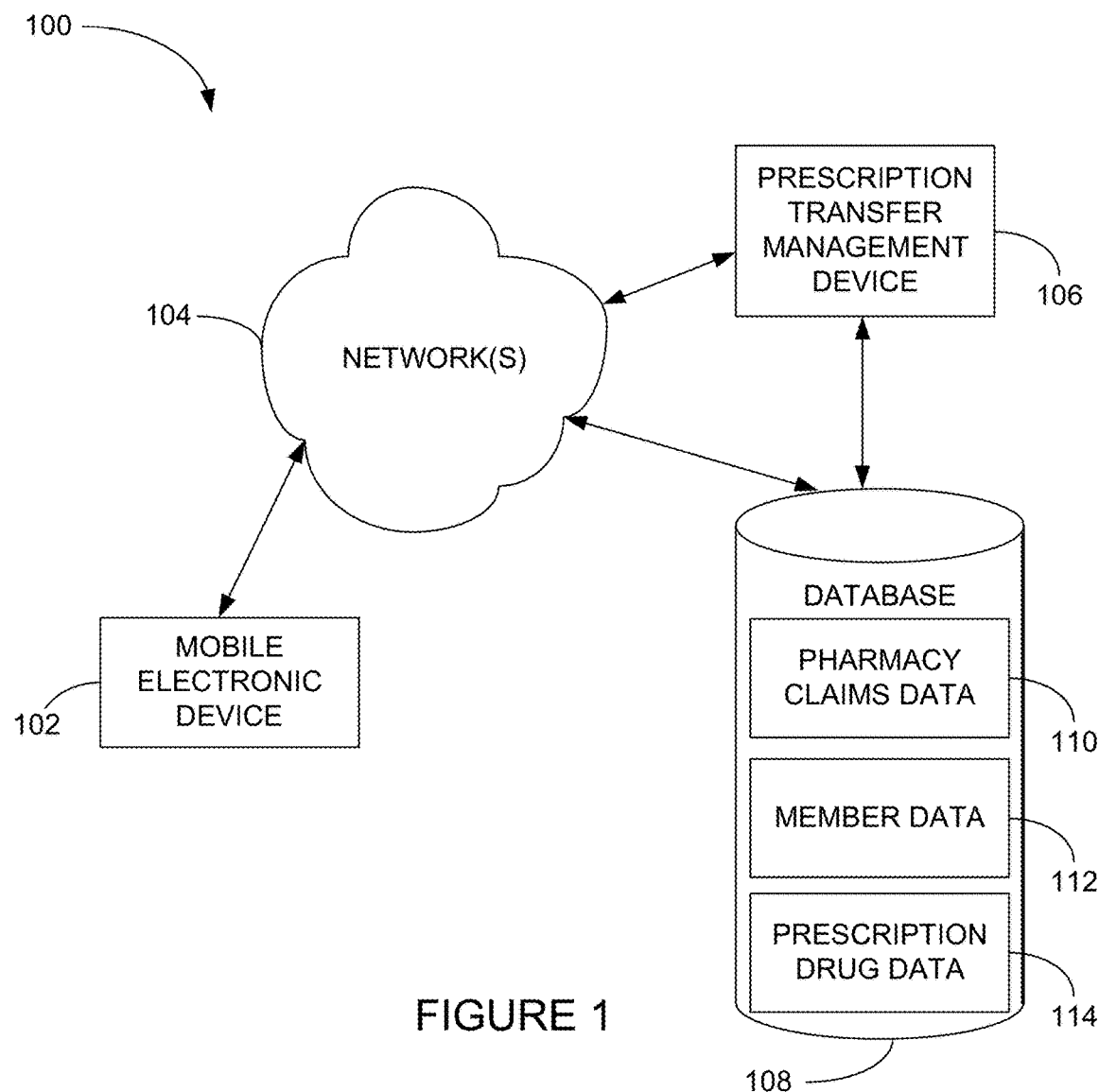
FIG. 1 is a block diagram of an example system, according to an example embodiment.

Example methods and systems for prescription transfer are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a member of a drug benefit program may initially fill a prescription for a drug prescribed by a physician or other care provider at retail pharmacy. In some instances, the care provider may prescribe a course of treatment that exceeds an amount of prescription drug that may be filled for the member at any one time. As such, the prescription may provide for a refill, in which the prescription may be filled one, or more than one, additional times, thereby providing the member with a sufficient quantity of the prescription drug for the prescribed course of treatment. For various reasons, the member may wish to have subsequent refills of the prescription filled by a mail order pharmacy. For example, receiving refills from a mail order pharmacy may provide a convenient way for the member to receive refills of the prescription, may be a cheaper way for the member to receive refills, may increase the likelihood that the member will stay adherent to the prescription, and the like.

A mail order pharmacy may fill or refill the prescription, and deliver the prescription drug to the member via a parcel service in accordance with an anticipated need, such as a time-wise schedule, or the like. As such, it may not be necessary for the member to visit the retail pharmacy store in person to have the prescription refilled and/or to pick up the refilled prescription. In addition to the convenience of receiving the refills of the prescription directly to the member's home or other designated location of delivery, the cost of the prescription drugs purchased through a mail order delivery pharmacy may be less than the cost of the same prescription drugs purchased from a retail pharmacy. The lower costs available through the mail order pharmacy may be the result, for example, of economies available to the mail order pharmacy that may be at least partially passed along to the member. The lower costs available through the mail order pharmacy may be the result of a lower co-pay required by the member according to a health care plan, under which the member may receive the prescription drugs. In addition, the member may be able to receive a greater amount of the prescription drug through mail order delivery as opposed to obtaining the fill of the prescription at a retail pharmacy. For example, the member may be eligible to receive a 90-day supply of prescription drug from the mail order pharmacy that the member would otherwise be able to receive a 30-day supply at the retail pharmacy.

In some embodiments, the member may capture an electronic image or other representation of a retail pharmacy prescription label for a prescription drug that the member wishes to have refilled by another pharmacy, for example, a mail order pharmacy. The retail pharmacy prescription label may be the label affixed to the container or packaging of the prescription drug received from the retail pharmacy. The electronic image of the retail pharmacy prescription label may include a representation of the retail pharmacy prescription number, or prescription number, for example in the form of a numeric string, a barcode, or the like. The member may transmit the electronic image to the mail order pharmacy via a mobile electronic device or otherwise to receive refills of the prescription drug from the mail order pharmacy. From the representation of the retail pharmacy prescription number, the mail order pharmacy may ascertain sufficient information to transfer refills of the prescription to the mail order pharmacy for home delivery of the refills to the member. As such, in some embodiments the member may request transfer of the prescription from the retail pharmacy to the mail order pharmacy by capturing an electronic image (e.g., a digital picture, a video clip, or the like) of the retail pharmacy prescription label and transmitting the electronic image to the mail order pharmacy (e.g., via text message, email, or the like).

In some embodiments, the member may capture the electronic image of the retail pharmacy prescription number using a mobile electronic device equipped with digital camera functionality. In some embodiments, the member may transmit the electronic image of the retail pharmacy prescription number to the mail order pharmacy using the mobile electronic device.

FIG. 1 is a block diagram of an example system 100, according to an example embodiment. The system 100 is an example environment in which a refill for a prescription may be transferred from a retail pharmacy to a mail order pharmacy. The system 100 includes a mobile electronic device 102 in communication with a prescription transfer management device 106 over a network 104.

For the purpose of illustration and description, the mobile electronic device 102 is generally used to facilitate the request for transfer of refills of the prescription from a first pharmacy (e.g., a retail pharmacy) to a second pharmacy (e.g., a mail order pharmacy). In some embodiments the mobile electronic device 102 may be used to capture the electronic image (e.g., digital picture, video clip, or the like) of the retail pharmacy prescription label and prescription number, and a separate device may be used to send the electronic image to the mail order pharmacy. Additionally, the device operator of the mobile electronic device 102 may be the member and/or may be an individual acting for the benefit of and/or on behalf of the member. Accordingly, while some illustrative embodiments may be described herein in which the device operator may be the member, it should be appreciated that the device operator may be an individual other than the member. Examples of such other individuals include parents, friends, guardians and caregivers.

In addition, while embodiments generally reflect that the prescription may be transferred from retail pharmacy to mail order pharmacy, the prescription may otherwise be transferred. For example, the prescription may be transferred to/or from a retail pharmacy or pharmacy network, a limited network retail pharmacy or pharmacy network, a mail order pharmacy, a dispending machine pharmacy, a specialty pharmacy, or the like.

The mobile electronic device 102 may be a stand-alone device that solely provides at least some of the functionality to enable the transfer of refills of the prescription from the retail pharmacy to the mail order pharmacy, or may be a multi-use device that has functionality outside of the functionality required to enable transfer of refills of the prescription as described herein. Examples of the mobile electronic device 102 include an IPHONE device by Apple, Inc., mobile electronic devices powered by ANDROID by Google, Inc., and a BLACKBERRY device by Research In Motion Limited. Other types of mobile electronic devices may also be used, including non-web-enabled cellular telephones, digital cameras, and the like. Additionally, while not shown, in some embodiments multiple electronic devices (including portable and generally not portable electronic devices) may be used to provide different aspects of the functionality to request transfer of refills of the prescription. Examples other such electronic devices may include personal computers, notebook computers, digital cameras, and the like.

The network 104 by which the mobile electronic device 102 communicates with the prescription transfer management device 106 may include, by way of example, Global System for Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The prescription transfer management device 106 is a device operated by an entity at least partially responsible for processing and/or generation of mail order delivery of prescription drugs. In some embodiments, the prescription transfer management device 106 may be operated by a mail order pharmacy. Further, in some embodiments, the prescription transfer management device 106 may be operated by other entities, which may operate the prescription transfer management device 106 on behalf of themselves, the mail order pharmacy, or another entity.

In general, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts and the like provided by the terms of the drug benefit program.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company. In various embodiments, the PBM may be the same entity as the mail order pharmacy, the PBM may be an entity related to the mail order pharmacy (e.g., through partial or complete common control, partial or complete common ownership or the like), and/or the PBM may be separate and discrete entity from the mail order pharmacy. In some embodiments, the methods and systems may generally be used to leverage prescription adjudication information controlled and/or managed by a pharmacy benefit manager to facilitate transferring prescriptions from a retail pharmacy to a mail order pharmacy.

Some of the operations of the PBM may include the following. A member or a person act on behalf of the member attempts to obtain a prescription drug at a retail pharmacy location of a pharmacy where the member can obtain drugs in a physical store from a pharmacist or pharmacist technician. The pharmacy can be associated with a single retail pharmacy location, or can be a pharmacy chain that includes multiple retail pharmacy locations. The pharmacy then submits a claim to the PBM. The PBM performs certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated.

The prescription transfer management device 106 may be in communication directly (e.g., through local storage) and/or through the network 104 (e.g., in a cloud configuration or software as a service) with a database 108. The database 108 may store one or more of pharmacy claims data 110 of a pharmacy benefit manager, member data 112, and prescription drug data 114. In some embodiments, the database 108, including the pharmacy claims data 110, may be controlled and/or operated by the PBM.

The pharmacy claims data 110 may include information maintained and/or created by, or on behalf, of the PBM regarding claims associated with members of a health plan relating to prescriptions that have been submitted by the member, or on behalf of the member, to a pharmacy to be filled. Examples of the pharmacy claims data 110 include member name, prescription number, issuing doctor, pharmacy name and contact information, and the like. In some embodiments, the foregoing may be captured each time a member has a claim for a prescription drug adjudicated. The pharmacy claims data 110 may include a client identifier that identifies the client of the PBM associated with the member and/or a member identifier that identifies the member to the client.

The member data 112 may include information related to members of the drug benefit program. Examples of member data may include member name, member date of birth, member address, member contact information (e.g., telephone numbers, address, email address, and the like). The prescription drug data 114 may include information regarding various prescription drugs.

While the system 100 in FIG. 1 is shown to include single devices 102, 106, multiple devices may be used. The devices 102, 106 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106 or in parallel to link the devices 102, 106.

Figure 2:
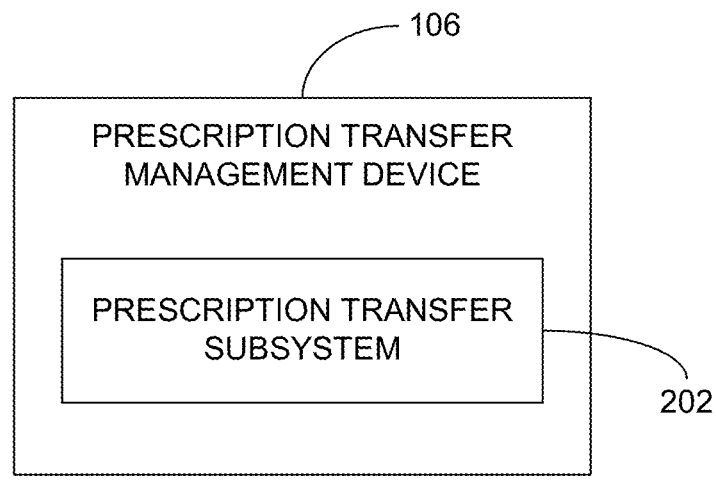
FIG. 2 is a block diagram of an example prescription transfer management device that may be deployed within the system of FIG. 1, according to an example embodiment.

FIG. 2 illustrates the prescription transfer management device 106, according to an example embodiment. The prescription transfer management device 106 may facilitate the transfer of a prescription from a pharmacy at which the prescription was originally filled to another pharmacy from which refills for the prescription may be obtained. The prescription transfer management device 106 may be deployed in the system 100, or may otherwise be used.

The prescription transfer management device 106 may include a prescription transfer subsystem 202. While the prescription transfer subsystem 202 will be described as a discrete subsystem for the purpose of explanation, the various functions of the subsystem may overlap with one or more other subsystems deployed on the prescription transfer management device 106 and/or be performed, at least in part, by other subsystems. For the purpose of description, the subsystem and modules of the prescription transfer subsystem 202 may be described as being embodied within a prescription transfer software application or suite. However, in some embodiments, one or more of the subsystem, modules, or both, may be fully, or partially, embodied in hardware and/or firmware, or may be fully, or partially, embodied in a separate software application or suite.

In general, the prescription transfer subsystem 202 may enable the transfer of a prescription from a source pharmacy (e.g., a retail pharmacy location) to a target pharmacy (e.g., a mail order pharmacy) for refills of the prescription.

Figure 3:
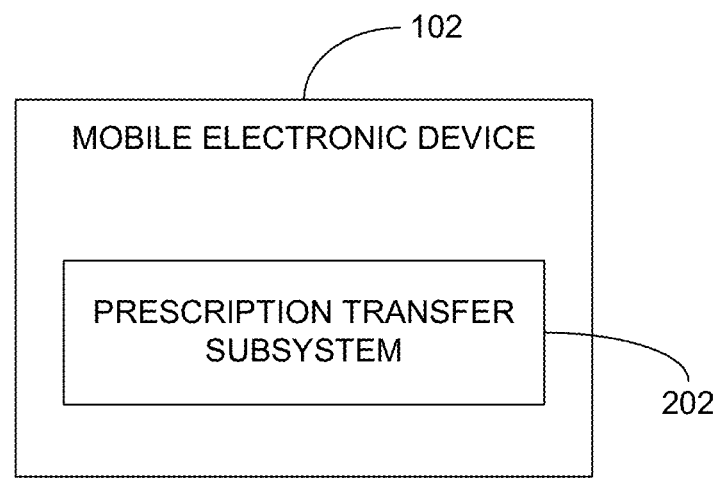
FIG. 3 is a block diagram of an example mobile computing device that may be deployed within the system of FIG. 1, according to an example embodiment.

FIG. 3 illustrates the mobile electronic device 102, according to an example embodiment. The mobile electronic device 102 may be deployed in the system 100, or may be otherwise used. The mobile electronic device 102 may include the prescription transfer subsystem 202. In some embodiments, the prescription transfer subsystem 202 may be deployed in both the prescription transfer management device 106 and the mobile electronic device 102. The mobile electronic device 102 may the perform some of the functionality, while other functionality is performed by the prescription transfer management device 106.

Figure 4:
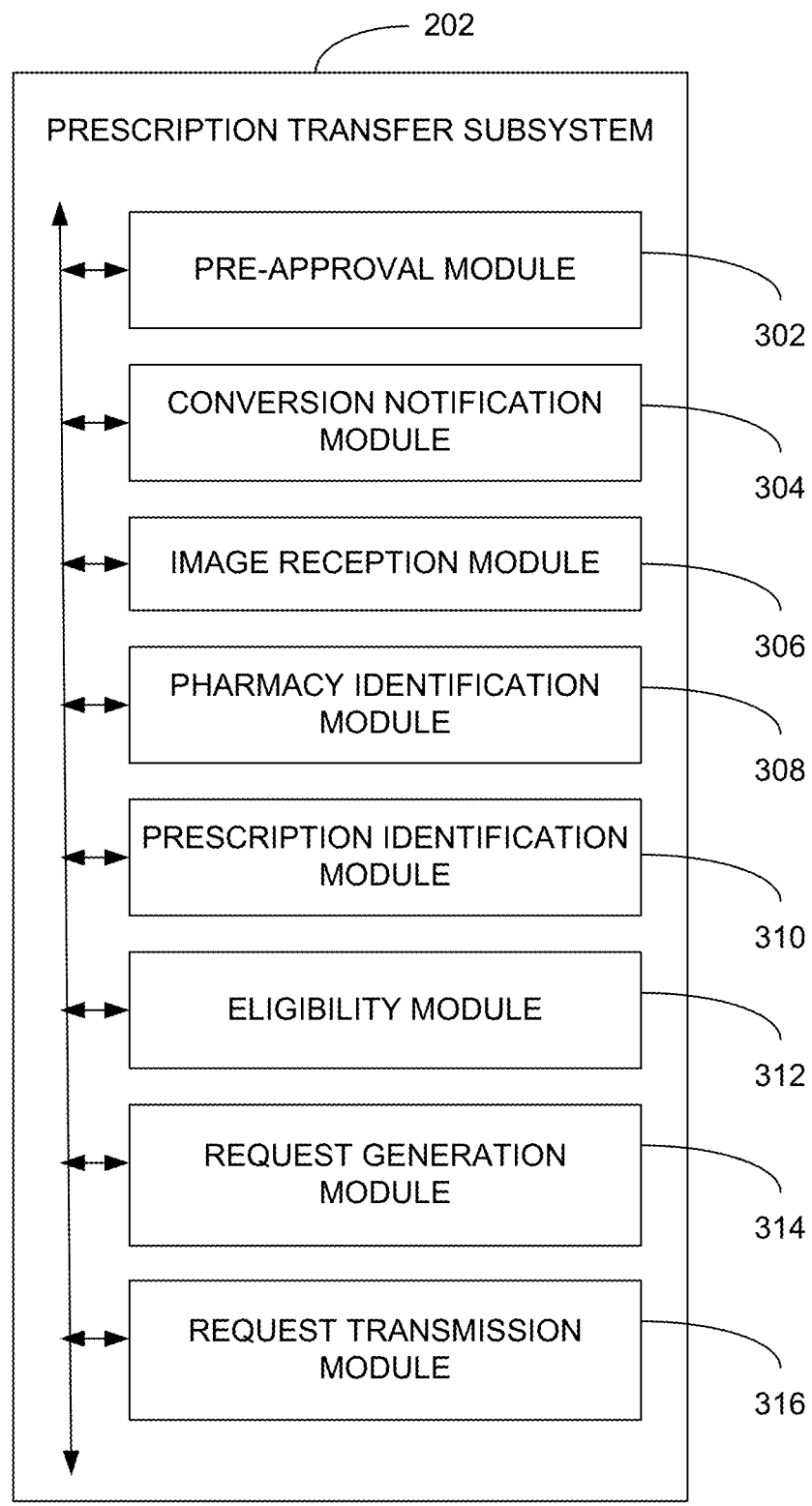
FIG. 4 is a block diagram of an example prescription transfer subsystem that may be deployed within the prescription transfer management device of FIG. 2, according to an example embodiment.

FIG. 4 illustrates an example embodiment of the prescription transfer subsystem 202 deployed in the prescription transfer management device 106, or otherwise deployed in another system, is shown including one or more modules communicatively coupled and included within the prescription transfer subsystem 202 to enable request of the transfer of a prescription from a source pharmacy to a target pharmacy for filling refills of the prescription. Modules of the prescription transfer subsystem 202 may include a pre-approval module 302, a conversion notification module 304, a image reception module 306, a pharmacy identification module 308, a prescription identification module 310, an eligibility module 312, a request generation module 314, and a request transmission module 316. Other modules may also be included.

In some embodiments, the modules of the prescription transfer subsystem 202 may be distributed so that some of the modules are deployed in the prescription transfer management device 106 and some of the modules are deployed in the mobile electronic device 102. In one embodiment, the modules are deployed in memory and executed by a processor coupled to the memory. The functionality contained within the modules 302-316 may be combined into a lesser number of modules, further divided among a greater number of modules, or redistributed among existing modules. Other configuration including the functionality of the modules 302-316 may be used.

In some embodiments, the pre-approval module 302 may enable preapproval to transfer a prescription to the target pharmacy to be obtained from the care provider of the member. In general, the pre-approval is sought prior to a request by the member to transfer the prescription. For example, the pre-approval module 302 may identify the care provider associated with a prescription for the member. In an example embodiment, the pre-approval module 302 may identify the care provider associated with a prescription based upon prescribing care provider information associated with an adjudicated prescription identified in the pharmacy claims data 110. The pre-approval module 302 may further obtain a pre-approval from the care provider to transfer the prescription. Obtaining the pre-approval to transfer the prescription may include transmitting a request to the care provider. The request may be automatically transmitted to the care provider by the pre-approval module 302. In some embodiments, the preapproval module 302 may initiate a work flow for another module or device to transmit the request and/or to prompt a representative of the target pharmacy to generate a request to transfer the prescription to the target pharmacy, and to transmit the request to the care provider. A response to the pre-approval to transfer the prescription to the target pharmacy may be received by the pre-approval module 302, e.g., as an electronic approval from the care provider and/or via an input (e.g., by a representative of the target pharmacy) in response to a received pre-approval from the care provider.

In some embodiments, the conversion notification module 304 may be deployed within the prescription transfer subsystem to enable a notification to be sent to the member indicating the possibility and/or necessity to transfer a prescription from the source pharmacy to the target pharmacy (e.g., from a retail pharmacy to a mail order pharmacy). For example, in an embodiment in which a preapproval request to transfer the prescription to mail order was transmitted by the pre-approval module 302, the conversion notification module 304 may transmit a notification to the member alerting the member that the prescription has been pre-approved for mail order delivery from the mail order pharmacy. The notification to the member may include, for example, a text message sent to a cellular telephone number associated with the member within one or more of the pharmacy claims data 110 and the member data 112, an automated, or in person, voice notification transmitted to a telephone number associated with the member, an email notification sent to the member at an email address associated with the member, and/or a written notification mailed to the member at an address associated with the member. The conversion notification may inform the member that the member may transfer the prescription to the mail order pharmacy by capturing an electronic image of a retail pharmacy prescription label associated with the prescription and sending the electronic image to prescription transfer management device 106 as a text message, a multi-media message, and email, or the like.

In some embodiments, the conversion notification module 304 determines whether the member is subject to mandatory home delivery and/or subject to a requirement to receive prescriptions by mail order after a certain number of prescription fills and/or refills at a retail pharmacy, e.g., based upon terms of a drug benefit program of the member. The conversion notification module 304 may determine whether the member is subject to being required to move to mail order or should be provided with an option to move to mail order based upon, at least in part, information included within one or both of the pharmacy claims data 110 and the member data 112. In some embodiments, the member must respond to the notification in order to not be blocked from filling the prescription drug by a particular type of source (e.g., retail pharmacy). If the conversion notification module 304 determines that the member is subject to home delivery, the conversion notification module 304 may transmit a conversion notification to the member inviting, and/or directing, the member to transfer a retail pharmacy prescription. The notification may inform the member that the member may transfer the prescription by capturing an electronic image of the retail pharmacy prescription label and sending the electronic image to the prescription transfer management device 106.

In some embodiments, the image reception module 306 receives an electronic image of a source pharmacy prescription label (e.g., a retail pharmacy prescription label) including a representation of a source pharmacy prescription number. In some embodiments, the image reception module 306 may receive the electronic image of the source pharmacy prescription label in response to a conversion notification transmitted to the member.

In an example embodiment, the member may use the mobile electronic device 102 to capture an electronic image of the source pharmacy prescription label including the representation of the source pharmacy prescription number, and the mobile electronic device may transmit the electronic image to the prescription transfer management device 106. The representation of the source pharmacy prescription number may include various types of representation, for example a barcode, a plain text numeric string, or the like. The image reception module 306 may receive the electronic image of the source pharmacy prescription label transmitted by the mobile electronic device 102.

For example, in some embodiments the member may take a digital picture or video clip of a source pharmacy prescription label (e.g., a retail pharmacy prescription label) on a bottle of prescription drugs that the member seeks to transfer from the source pharmacy to a target pharmacy (e.g., a mail order pharmacy). In some embodiments, the mobile electronic device 102 may include functionality of a cellular telephone including a digital camera. In such an embodiment, the mobile electronic device 102 may capture an electronic image of the source pharmacy prescription label on the bottle of prescription drugs, in which the electronic image includes a representation of the source pharmacy prescription number (e.g., which may include a barcode, a plain text numeric string, or the like). The mobile electronic device 102 may transmit the electronic image to the prescription management device 106. For example, in some embodiments the mobile electronic device 102 may transmit the electronic image of the source pharmacy prescription label as a text message (e.g., a short message service message) or multimedia message (e.g., a multimedia messaging service message). In some embodiments, the mobile electronic device 102 may transmit the electronic image of the source pharmacy prescription label to the prescription transfer management device 106 as an email or an attachment to an email. In some embodiments, the mobile electronic device 102 may execute a stand-alone application that may, for example, communicate with the prescription management device 106. In such an embodiment, the application may transmit the electronic image of the source pharmacy prescription label to the prescription management device 106. In some embodiments, the mobile electronic device 102 may capture an electronic image of the source pharmacy prescription label, and a second device may transmit the electronic image of the source pharmacy prescription label as a text message, multimedia message, email, and/or attachment to an email. As such, the request to transfer the prescription to the target pharmacy may be made by capturing an electronic image of the source pharmacy prescription label (e.g., the retail pharmacy prescription label) on a bottle of prescription drugs that the member wishes to receive from the target pharmacy (e.g., from the mail order pharmacy), and transmitting the electronic image to the prescription transfer management device 106 in order to receive refills of the prescription from the target pharmacy.

Consistent with the forgoing, the image reception module 306 may be coupled with one, or more than one, reception interfaces. For example, the image reception module 306 may directly, and/or indirectly, interface with a short message service gateway for receiving text messages and/or multimedia messages from electronic devices (e.g., the mobile electronic device 102) associated with members. Similarly, the image reception module 306 may directly and/or indirectly interface with an email server for receiving email messages transmitted by electronic devices, such as the mobile electronic device 102, associated with members. The image reception module 306 may be coupled with various additional/alternative interfaces for receiving electronic images from electronic devices (such as the mobile electronic device 102) associated with members.

Figure 11:
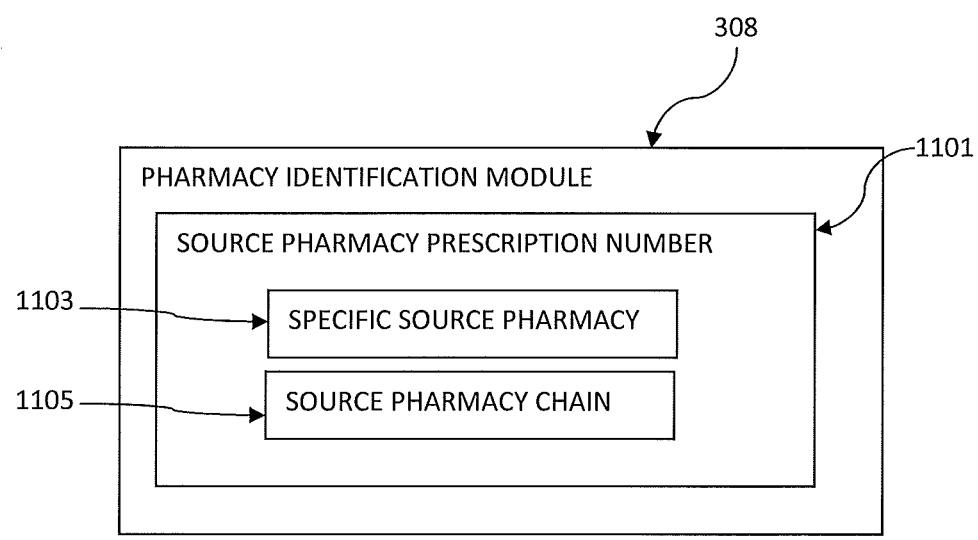
FIG. 11 is a block diagram of a pharmacy identification module, according to an example embodiment.

The pharmacy identification module 308 may, in some embodiments, enable the pharmacy associated with the source pharmacy prescription label to be identified. For example, the source pharmacy prescription number 1101 (FIG. 11) may generally include a number that is unique to the specific source pharmacy 1103 (FIG. 11) and/or may include a number that is unique to a specific chain of commonly owned and/or operated retail pharmacies 1105 (FIG. 11). However, in some embodiments, the source pharmacy prescription number may not be directly and/or universally indicative of the prescription. Accordingly, in some embodiments identifying the source pharmacy may facilitate identifying the prescription associated with the member based upon the source pharmacy prescription number included in the electronic image of the source pharmacy prescription label.

In some embodiments, the pharmacy identification module 308 may identify the source pharmacy based upon information included in the electronic image of the source pharmacy label. For example, the electronic image of the source pharmacy prescription label may include information such as a name of the source pharmacy, an address of the source pharmacy, a logo associated with the source pharmacy, and a telephone number associated with the source pharmacy, as well as various additional and/or alternative indicia or other information. The pharmacy identification module 308 may utilize image recognition (e.g., optical character recognition, and the like) to identify the source pharmacy based upon information included in the electronic image of the source pharmacy prescription label.

In some embodiments, the pharmacy identification module 308 may identify the source pharmacy by determining member identification data, and querying the database 108 including pharmacy claims data 110 and member data 112 relative to the member identification data. Member identification data may include any information that may be used to identify the prescription associated with the member within the database 108 including the pharmacy claims data 110 and member data 112. For example, the member identification data may include one, or more than one, of a member name, a member data of birth, a member address, a name of the prescribing care provider, a member telephone number, and a member email address, as well as various other information. In some embodiments, the member identification data may not directly identify the member. However, the member identification data may be associated with the source pharmacy within the database 108 including pharmacy claims data 110 and member data 112, and serve to identify a particular source pharmacy associated with the member.

In some embodiments, member identification data may be determined based upon the electronic image of the source pharmacy prescription label received by the image reception module 306. For example, if the electronic image of the source pharmacy prescription label was transmitted as a text message or a multimedia message from a cellular telephone, the pharmacy identification module 308 and/or the image reception module 306 may determine the telephone number from which the electronic image was transmitted based upon a caller ID associated with the text message or multimedia message. Further, in some embodiments the name of the member may be determined based upon a reverse look-up of the telephone number from which the text message or the multimedia message was transmitted. In an embodiment in which the electronic image was transmitted as an e-mail, the pharmacy identification module 308 and/or the image reception module 306 may determine an e-mail address and/or a name of the member based upon a sender e-mail address from which the electronic image was sent. Member identification data, such as cellular telephone number, e-mail address, and member name may be included in one or both of the pharmacy claims data 110, e.g., as part of member data associated with a claim that was adjudicated, and the member data 112. In such an embodiment, the pharmacy identification module 308 may query the database 108 including the pharmacy claims data 110 and the member data 112 relative to the cellular telephone number, e-mail address, and/or member name to identify the source pharmacy at which the member filled the prescription.

In some embodiments, the pharmacy identification module 308 may determine member identification data by performing image recognition of plain text information included in the electronic image of the source pharmacy prescription label. For example, in addition to the representation of the source pharmacy prescription number, the electronic image of the source pharmacy prescription label may include information such as the name of the member, the address of the member, the name of the prescribing care provider, a name of the drug, and the like. One or more of such pieces of member identification data may be included within the electronic image of the source pharmacy prescription label. The pharmacy identification module 308 may utilize image recognition (e.g., optical image recognition, and/or similar techniques) to determine one or more pieces of member identification data included in the electronic image of the retail pharmacy prescription label. The retail pharmacy identification module 308 may query the database 108 including pharmacy claims data 110 and member data 112 relative to the pharmacy prescription number and relative to one or more pieces of member identification data determined by the retail pharmacy identification module 308.

The prescription identification module 310 may identify a prescription associated with the representation of the source pharmacy prescription number. In some embodiments, the prescription identification module 310 may determine the source pharmacy prescription number indicated by the representation of the source pharmacy prescription number included within the electronic image of the source pharmacy prescription label, and may identify the prescription associated with that source pharmacy prescription number. The prescription may include, for example, the prescription drug, the dosage, and administration instructions (e.g., twice daily by mouth) as indicated by the care provider.

Various pharmacies may use different mechanisms to represent the pharmacy prescription number on their respective prescription pharmacy label included on the bottle or other container or packaging of the prescription drug. For example, the retail prescription pharmacy may include a plain text numeric string and/or an alphanumeric string. The source pharmacy prescription label may also and/or alternatively include a barcode representation of the source pharmacy prescription number on the label. In an embodiment in which the representation of the source pharmacy prescription number includes a plain text numeric string the prescription identification module 310 may perform image recognition on the electronic image of the plain text numeric string to generate the source pharmacy prescription number. In an embodiment in which the representation of the source pharmacy prescription number includes a barcode, the prescription identification module 310 may decode the electronic image of the barcode to generate the source pharmacy prescription number.

In some embodiments, the prescription identification module 310 may identify the prescription by querying the database 108 including pharmacy claims data 110 of a PBM based upon the source pharmacy prescription number and the source pharmacy identified by the pharmacy identification module 308. The pharmacy claims data 110 may include an association between the source pharmacy, the source pharmacy prescription number and the prescription issued to the member by the prescribing care provider. The pharmacy claims data 110 may include, for example, one, or more than one, of a member name, the prescription, a member ID, a billing log, a national drug code for the prescription drug, a date on which the prescription was last filled, and a member drug history. Various additional and/or alternative information may also be included within the pharmacy claims data 110 of the PBM.

In some embodiments, in addition to using member identification data to identify the source pharmacy and/or the prescription, the prescription identification module 310 may, as a safety precaution (e.g., to increase the likelihood that a correct prescription is prepared for the member), verify that a prescription identified by the query of the pharmacy claims data 110 corresponds to the prescription for the member. In some embodiments, verifying that the prescription identified by the query of the pharmacy claims data 110 corresponds to the prescription for the member may utilize a multi-point congruence of information. For example, a result including the source pharmacy prescription number and one or more of a member name, a member date of birth, a time frame during which the prescription was issued, and a name of the prescribing care provider may provide a desired level of confidence that the prescription identified by the prescription identification module 310 is the prescription for the member.

In some embodiments, the eligibility module 312 may determine whether the prescription is eligible to be transferred from the source pharmacy to the target pharmacy. In some embodiments, the eligibility of the prescription to be transferred from the source pharmacy to the target pharmacy may be based on one, or both, of the eligibility of the prescription to be refilled, and the eligibility of the prescription drug associated with the prescription to be provided by the target pharmacy.

For example, and as generally discussed above, in the event that a prescribed course a treatment may require a greater quantity of a prescription drug than may be dispensed at a single time, the prescription may include one, or more than one, refills to accommodate the prescribed course of treatment. Further, in some situations the member may be required to visit the prescribing care provider before additional refills can be made. Accordingly, in some embodiments, the eligibility module 312 may determine whether the prescription is eligible for a refill, including whether the prescription includes any available refills before the member returns to the care provider to receive an additional prescription. In some embodiments, the eligibility module 312 may determine whether the prescription is eligible for a refill, including determining when the prescription was last refilled. For example, some prescriptions may not be filled within a defined time period since the prescription was last filled and/or some prescriptions may not be filled outside of a defined period since the prescription was last filled. Further, in an example in which the target pharmacy includes a mail order pharmacy, the eligibility module 312 may compare the date the prescription was last filled with a proposed mail date of a mail order refill to determine whether the current supply of prescription drugs (e.g., based on the last fill date of the prescription and the anticipated duration of the last fill of the prescription) will last until the proposed mail date of the mail order refill. In the event that the prescription is not eligible for a refill, in some embodiments, an alert may be transmitted to the member, e.g., to the telephone number or email address from which the electronic image was received.

In some embodiments, the eligibility of the prescription drug to be transferred may be based upon, for example, terms of a health plan of the member and/or regulations regarding, for example, mail order delivery of prescription drugs. In some embodiments, in the event that the prescription drug associated with the prescription is not eligible for mail order delivery, the eligibility module 312 may generate an alert indicating the non-eligibility of the prescription drug for home delivery. The alert indicating the non-eligibility of the prescription drug for home delivery may be transmitted to the member, for example in the form of a text message, automated voice call, or email transmitted to the telephone number or email address from which the electronic image of the source pharmacy prescription label was received. In some embodiments, the alert generated by the eligibility module 312 may motivate a customer service representative of the target pharmacy to contact the member to inform the member that the prescription drug is not eligible for refill by the target pharmacy, or not eligible for mail order delivery.

In some embodiments, when the eligibility module 312 determines that the drug is not eligible refill by the target pharmacy (e.g., the drug is not eligible for mail order delivery), the eligibility module 312 may generate a request to the prescribing care provider requesting that the prescription be changed from the prescribed drug to a new drug that is eligible for refill by the target pharmacy. The new drug may include a suitable substitute drug that may be eligible for refill by the target pharmacy (e.g., eligible for mail order delivery).

In some embodiments, if the eligibility module 312 determines that the prescribed drug is not eligible for refill by the target pharmacy, the eligibility module 312 may determine if a chemically equivalent drug exists. If a chemically equivalent drug exists, the eligibility module 312 may further determine whether the chemically equivalent drug is eligible for refill by the target pharmacy. If the chemically equivalent drug is eligible for refill by the target pharmacy, the eligibility module 312 may identify the chemically equivalent drug for the refill of the prescription. In some embodiments, a refill may include a prescription drug from the target pharmacy in response to a received electronic image of the source pharmacy prescription label including the source pharmacy prescription number. As such, in some embodiments a prescription drug that is not the same as, but is chemically equivalent to, or a suitable substitute for, the prescription drug associated with the source pharmacy prescription number may be deemed a refill.

The request generation module 314 may generate a request for a refill of the prescription (e.g., a request for a refill of the prescription by mail order delivery). In some embodiments, the request generation module 314 may generate a request to transfer the prescription from the source pharmacy to the target pharmacy. In some embodiments the request generation module 314 may pre-populate at least a portion of a prescription to transfer the prescription from the source pharmacy to the target pharmacy. For example, the information regarding the prescription included within the pharmacy claims data 110 of the PBM may include the member name, date of birth, drug being prescribed, dosage, name of the prescribing care provider and the like. The request generation module 314 may extract information necessary to pre-populate at least a portion of a prescription for the member to be filled by the target pharmacy. In some embodiments, one or more of the pieces of information necessary to pre-populate the prescription may additionally/alternatively be determined based upon the electronic image of the source pharmacy prescription label, e.g., by using image recognition. In the event that any pieces of information that cannot be pre-populated based upon information determined from the pharmacy claims data 110 and/or the electronic image of the source pharmacy prescription label, such additional information may be provided by a representative of the target pharmacy and/or the prescribing care provider. The at least partially pre-populated prescription may be forwarded, e.g., in hard copy or electronic form, to the prescribing care provider for the required care provider authorization, thereby allowing the prescription to be filled by the target pharmacy. Accordingly, in some embodiments the request generation module 314 may generate a request that may include a pre-populated prescription to be signed by the prescribing care provider.

As discussed above, in some embodiments, in which the prescription drug associated with the prescription may not be eligible for refill by the target pharmacy (e.g., may not be eligible for mail order delivery), a request may be transmitted to the prescribing care provider to switch the member to a suitable substitute prescription drug that may be eligible refill by the target pharmacy. In an embodiment in which the prescribing care provider provides authorization to switch the member to a suitable substitute prescription drug that is eligible for refill by the target pharmacy, the request generation module 314 may generate a request for the suitable substitute prescription drug. In an embodiment in which a chemically equivalent prescription drug exists for the prescription drug, the request generation module 314 may generate request for the chemically equivalent prescription drug.

In some embodiments, the request generation module 314 may identify a transmission source associated with the electronic image. The transmission source may include, for example, a cellular telephone number associated with the mobile electronic device, an email address associated with the member, or the like. The request generation module 314 may also verify that the transmission source is associated with the member. The request generation module 314 may verify that the transmission source is associated with the member by, for example, comparing the transmission source with information included within the pharmacy claims data 110, or other similar data. The request to transfer the prescription may be based upon the verification that the transmission source is associated with the member.

In some embodiments, the request generation module 314 may schedule a mail order delivery based upon a prior fill data for the prescription. For example, the pharmacy claims data 110 may include data indicating the data on which the prescription was last filled (e.g., when the prescription was originally filled, and/or when the prescription was most recently refilled). The request generation module 314 may schedule the refill of the prescription by the mail order pharmacy such that the refill of the prescription may be delivered to the member prior to an anticipated time at which the existing supply of prescription drugs may be exhausted. For example, if the member last filled the prescription on May 23$^{rd}$ and the prescription provides for a one month supply of prescription drugs, the request generation module 314 may schedule the refill of the prescription to be delivered to the member prior to June 23$^{rd}$. Similarly, if earliest time at which the mail order delivery may be scheduled (e.g., due to delays in transacting the transfer, etc.) is later than the anticipated time at which the existing supply of prescription drugs may be exhausted, the request generation module 314 may generate an alert indicating that the member must refill the prescription at a retail pharmacy store. In some embodiments, the alert generated by the request generation module 314 may be automatically transmitted to the member, for example via a text message, automated voice call, or email directed to a telephone number or email address from which the electronic image of the source pharmacy prescription label was received. In other embodiments, the alert may motivate a customer service representative of the target pharmacy to contact the member.

In some embodiments, the request transmission module 316 may transmit the request to the member. The member may, for example, communicate the request to transfer the prescription to the target pharmacy to the care provider, e.g., at a next appointment with the care provider, via fax, or other suitable method. In some embodiments, the request transmission module 316 may transmit the request to the care provider associated with the prescription. The care provider associated with the prescription may include, for example, the member's regular doctor, a special doctor (such as a hospital doctor or specialty doctor) or other care provider that can prescribe drugs.

Figure 5:
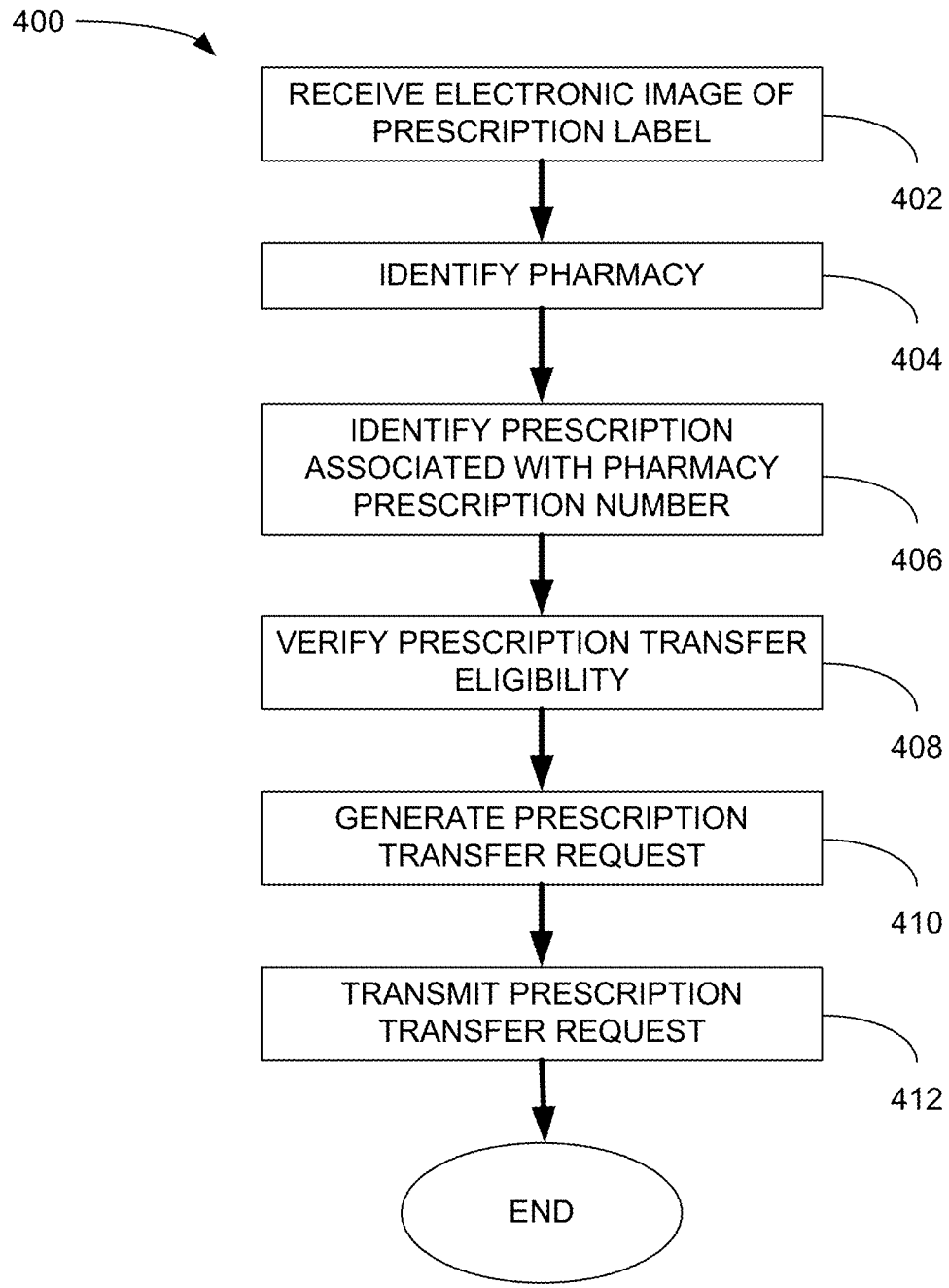
FIGS. 5 and 6 are block diagrams of flowcharts illustrating methods for prescription transfer, according to example embodiments.

FIG. 5 illustrates a method 400 for transferring a prescription to delivery target pharmacy according to an example embodiment. The method 400 may be performed by the prescription transfer management device 106, or may be otherwise performed.

An electronic image of a source pharmacy prescription label, including a representation of a source pharmacy prescription number, is received at block 402. The source pharmacy prescription label may be a label affixed to a container of a prescription drug by the source pharmacy (e.g., a retail pharmacy). Generally, the representation of the source pharmacy prescription number may be, for example, a plain text numeric string or barcode representing the unique number assigned by the source pharmacy to the particular prescription.

In some embodiments, the electronic image of the source pharmacy prescription label may include a digital picture, video clip, of the source pharmacy prescription label. The electronic image of the source pharmacy prescription label may be received from an electronic device (e.g., the mobile electronic device 102) associated with a member as a text message, a multimedia message, an email (and/or an attachment to an email), or through other similar means from the member. In some embodiments, the mobile electronic device 102 may include, for example, a cellular telephone including a digital camera. In other embodiments, the electronic image of the source pharmacy prescription label may be received from another computing device associated with the member.

A source pharmacy associated with the prescription may be identified at block 404. In some embodiments, identifying the source pharmacy may include identifying the source pharmacy based upon information included within the electronic image of the source pharmacy prescription label, e.g., using image recognition. Information included within the source pharmacy prescription label may include, for example, a source pharmacy name, a source pharmacy phone number, a source pharmacy address, and a source pharmacy logo.

In some embodiments, identifying the source pharmacy associated with the prescription may include identifying member information, such as member name, member date of birth, member address, and the like. The member information may be identified from information included within the source pharmacy prescription label using image recognition, or other suitable techniques. The database 108 including pharmacy claims data 110 may be queried based upon the member information to identify the source pharmacy associated with the prescription.

A prescription associated with the source pharmacy prescription number may be identified at block 406. In some embodiments, identifying the prescription associated with the source pharmacy prescription number may include determining the source pharmacy prescription number from the representation of the source pharmacy prescription number included within the electronic image. In some embodiments, determining the source pharmacy prescription number from the representation of the source pharmacy prescription number may include, for example, performing image recognition on the representation of the source pharmacy prescription number (e.g., in an embodiment in which the representation of the source pharmacy prescription number includes a plain text numeric string) or decoding a barcode (e.g., in an embodiment in which the presentation of the source pharmacy prescription number includes a barcode).

The retail pharmacy prescription number may include querying the database 108 including source pharmacy prescription number may include querying pharmacy claims data 110 of a PBM relative to the source pharmacy prescription number and the identity of the source pharmacy.

The eligibility of the prescription to be refilled by the target pharmacy may be verified at block 408. In some embodiments, verifying the eligibility of the prescription for refill by the target pharmacy may include determining whether the prescription is eligible for refills. In some embodiments, determining whether the prescription is eligible for refills may include determining when the prescription was last filled. In some embodiments, determining whether the prescription is eligible for refills may include determining if the prescription includes any further refills before the member must visit the prescribing care provider.

In some embodiments, verifying the eligibility of the prescription to be refilled by the target pharmacy may include determining if the prescription drug is eligible for mail order delivery. In some embodiments, if the prescription drug is not eligible for mail order delivery (or is not otherwise eligible to be refilled by the target pharmacy), a request to switch the member to a suitable substitute drug may be transmitted to the prescribing care provider. In some embodiments, the prescription drug associated with the prescription may be switched to a chemically equivalent prescription drug that is eligible for refill by the target pharmacy (e.g., eligible for mail order delivery).

A request may be generated at block 410 for a refill of the prescription by the target pharmacy. In some embodiments, generating the request may include verifying that the identified prescription is the prescription associated with the member. In some embodiments, generating the request may include verifying that a transmission source of the electronic image is associated with the member. In some embodiments, generating the request may include generating a request for a suitable substitute prescription drug or a chemically equivalent prescription drug.

In some embodiments, generating the request for a refill of the prescription may include pre-populating at least a portion of a new prescription. Pre-populating the new prescription may include populating the prescription with information obtained from the pharmacy claims data 110 and/or with information obtained from the electronic image of the source pharmacy prescription label, e.g., which may be obtained through image recognition of plain text included on the source pharmacy prescription label.

In some embodiments, generating the request may include scheduling a mail order delivery of the refill of the prescription based upon prior fill data for the prescription. The prior fill date for the prescription may be used in conjunction with prescription details, such as a quantity of the prescription and a prescribed dosage of the prescription drug, to determine an anticipated time at which the refill may be required by the member to maintain continuity of treatment according to the prescription.

The request may be transmitted at block 412. Transmitting the request may include transmitting the request to the member. In some embodiments, transmitting the request may include transmitting the request to the care provider associated with the prescription.

Figure 6:
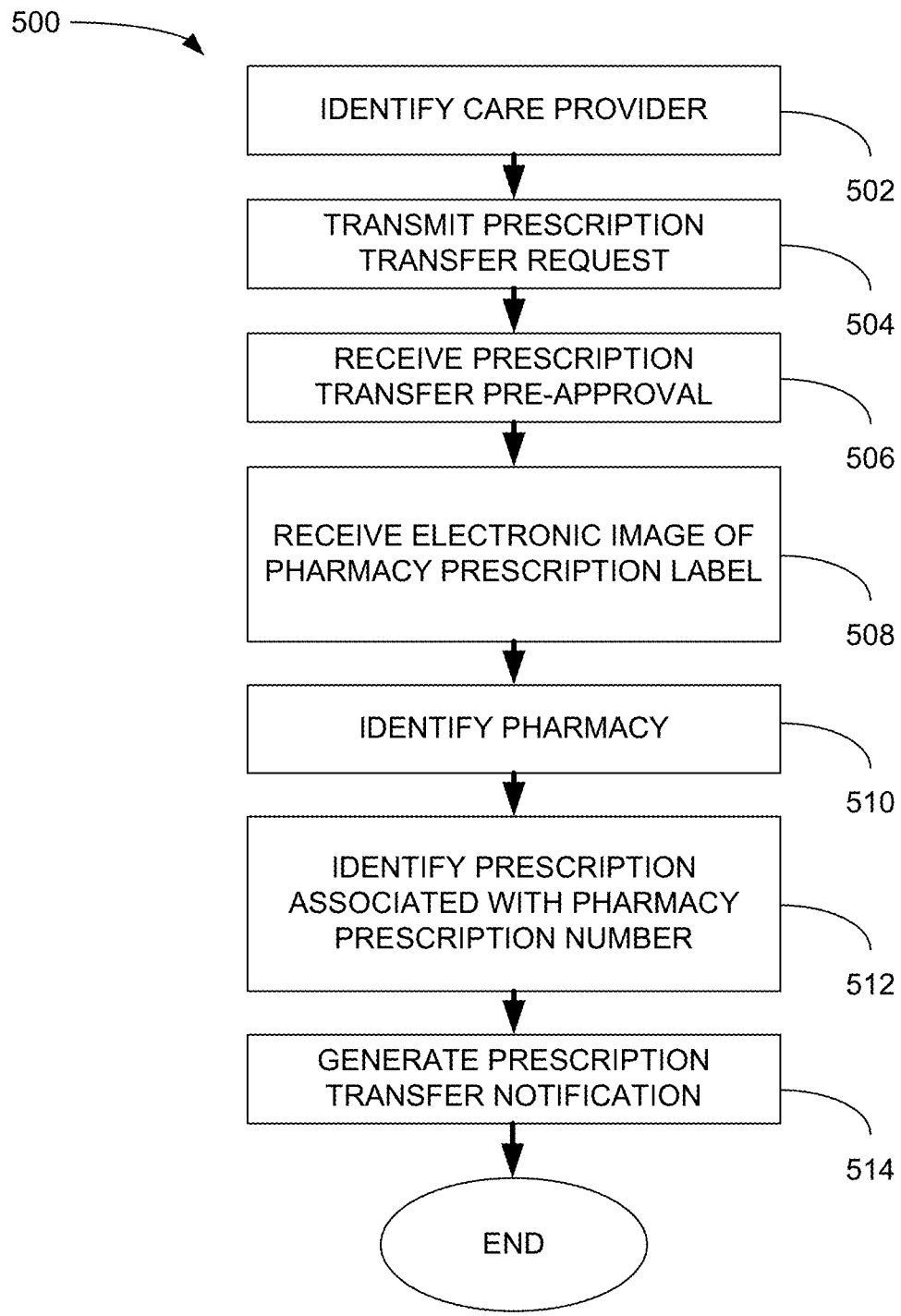

FIG. 6 illustrates a method 500 for transferring a prescription to a target pharmacy according to an example embodiment. The method 500 may be performed by the prescription transfer management device 106, or may be otherwise performed.

An identity of a care provider associated with a prescription may be determined at block 502. The identity of the care provider may include a doctor or other individual who issued a prescription. In some embodiments, the care provider may be identified based upon the pharmacy claims data 110 of a PBM.

A request to transfer the prescription to a target pharmacy may be transmitted to the care provider at block 504. The request may request the approval of the care provider to transfer the prescription to the target pharmacy. In some embodiments, the request may include a request to switch a prescription drug to a suitable substitute drug that is eligible for refill by the target pharmacy (e.g., eligible for mail order delivery). In some embodiments, in response to receiving an approval of the request from the care provider, a transfer notification may be transmitted to the member associated with the prescription. The transfer notification may indicate that the member may transfer the prescription to the target pharmacy by sending an electronic image of the source pharmacy prescription label to the prescription transfer management device 106.

In some embodiments, the transfer notification may inform the member that the member has been pre-approved to transfer the prescription to the target pharmacy. In some embodiments, e.g., based upon a health care plan associated with the member, or the like, the transfer notification may inform the member that the member is required to transfer the prescription to the target pharmacy (e.g., to mail order delivery).

The electronic image of the source pharmacy prescription label may be received at block 508. The source pharmacy prescription label may be a label affixed to a container of a prescription drug by a source pharmacy. Generally, the representation of the source pharmacy prescription number may be, for example, a plain text numeric string or barcode representing the unique number assigned by the source pharmacy to the particular prescription.

In some embodiments, the electronic image of the source pharmacy prescription label may include a digital picture, video clip, or the like, of the source pharmacy prescription label. The electronic image of the source pharmacy prescription label may be received as a text message, a multimedia message, an email (and/or an attachment to an email), or through other similar. In some embodiments, the electronic image of the source pharmacy prescription label may be transmitted by the mobile electronic device 102, which may include, for example, a cellular telephone including a digital camera functionality. In other embodiments, the electronic image of the source pharmacy prescription label may be received from another computing device.

The source pharmacy associated with the source pharmacy prescription label may be identified at block 510. In some embodiments, identifying the source pharmacy may include identifying the source pharmacy based upon information included within the electronic image of the source pharmacy prescription label, e.g., using image recognition. Information included within the source pharmacy prescription label may include, for example, a source pharmacy name, a source pharmacy phone number, a source pharmacy address, and a source pharmacy logo.

In some embodiments, identifying the source pharmacy associated with the prescription may include identifying member information, such as member name, member date of birth, member address, and the like. The member information may be identified from information included within the source pharmacy prescription label using image recognition, or other suitable techniques. The database 108 including pharmacy claims data 110 may be queried based upon the member information to identify the source pharmacy associated with the prescription.

The prescription associated with the source pharmacy prescription number and the identified source pharmacy may be identified at block 512. In some embodiments, identifying the prescription associated with the source pharmacy prescription number may include determining the source pharmacy prescription number from the representation of the source pharmacy prescription number included within the electronic image. In some embodiments, determining the source pharmacy prescription number from the representation of the source pharmacy prescription number may include, for example, performing image recognition on the representation of the source pharmacy prescription number (e.g., in an embodiment in which the representation of the source pharmacy prescription number includes a plain text numeric string) or decoding a barcode (e.g., in an embodiment in which the presentation of the source pharmacy prescription number includes a barcode).

In some embodiments, identifying the prescription associated with the source pharmacy prescription number may include querying the database 108 including pharmacy claims data 110 of a PBM relative to the source pharmacy prescription number and the identity of the source pharmacy.

A conversion notification may be generated at block 514. The conversion may notify the member that the prescription has been transferred to the target pharmacy. In some embodiments, the conversion notification may include a notification transmitted by text message, email, in writing, or the like.

Figure 7:
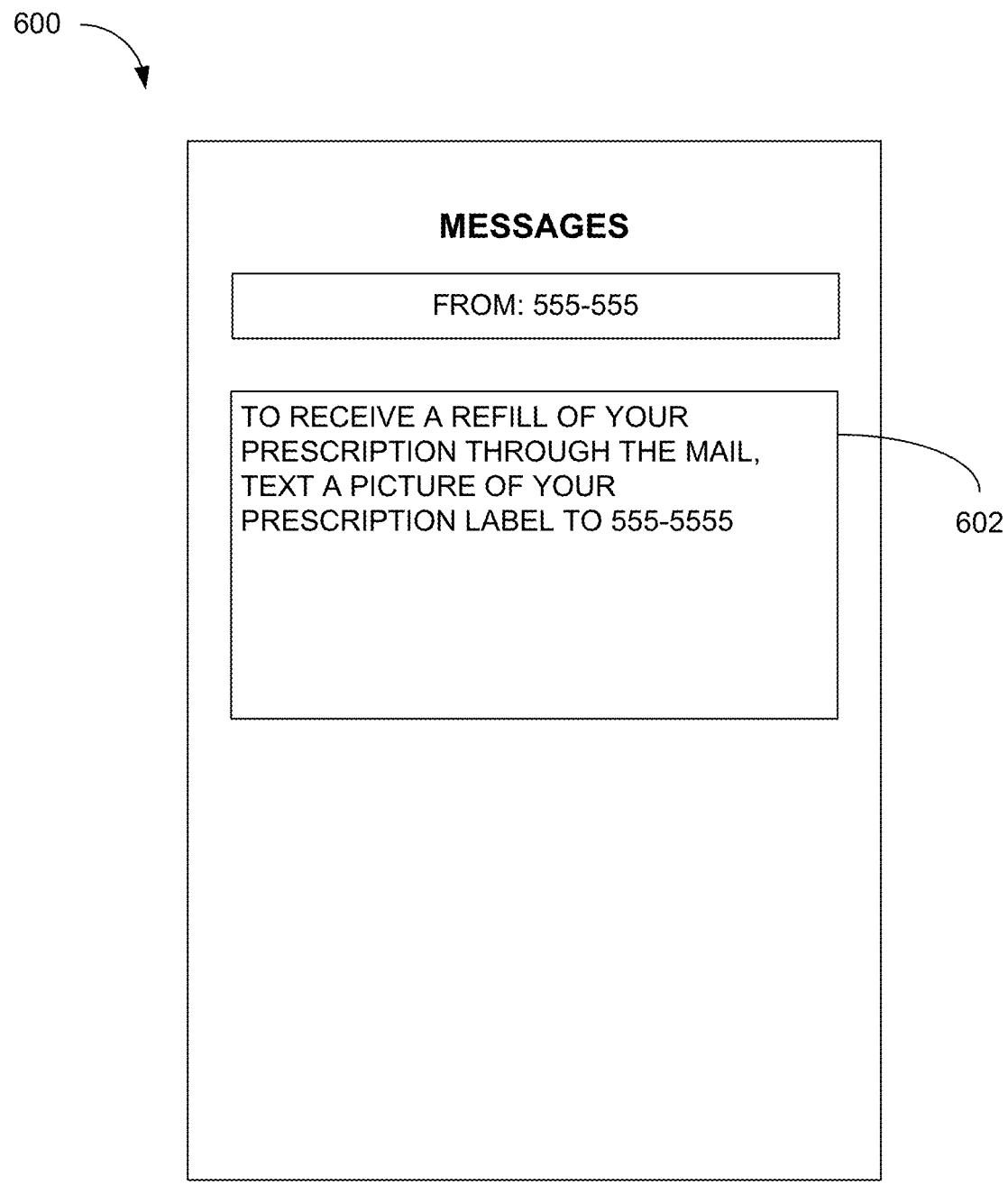
Figure 8:
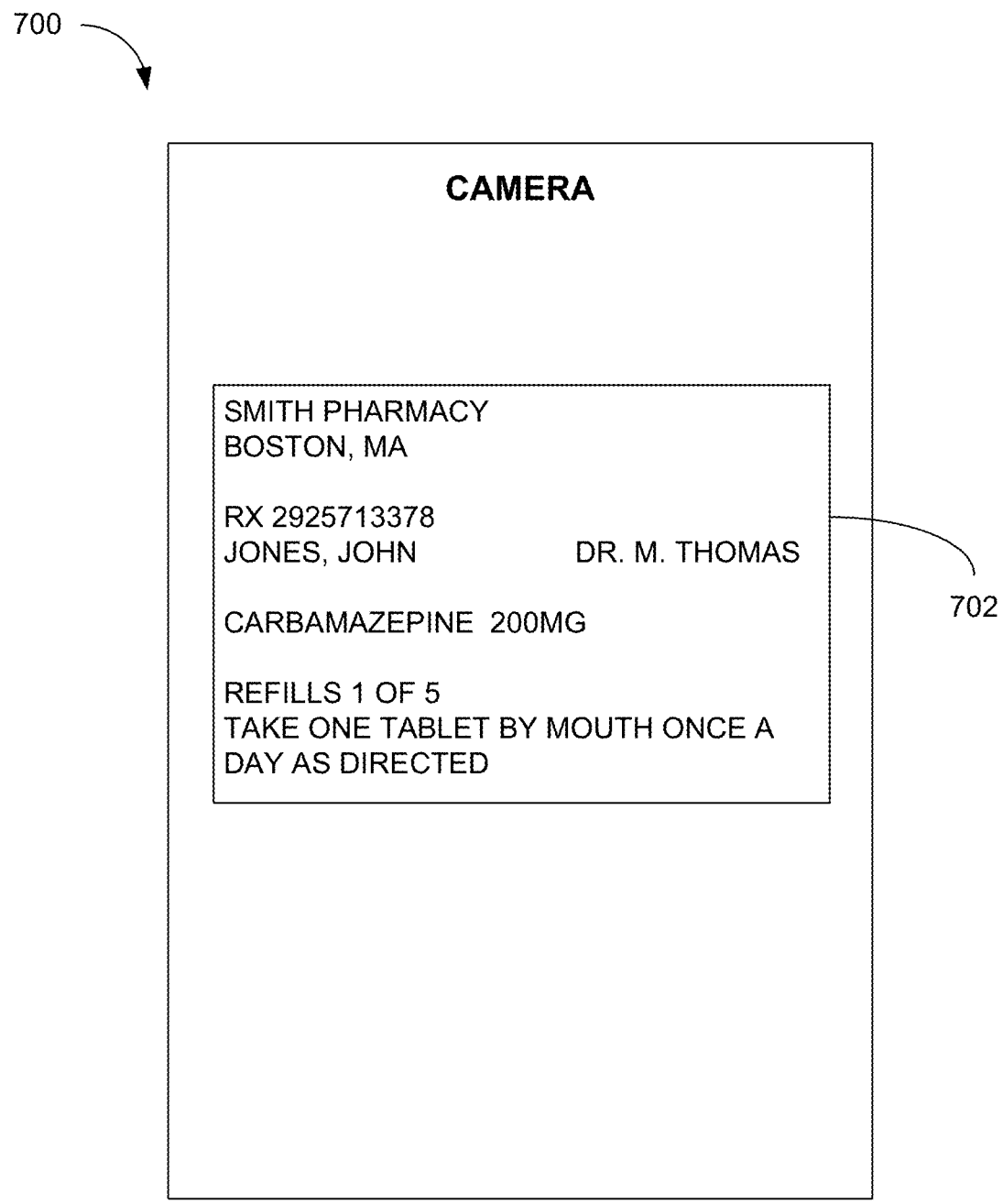

FIGS. 7-9 are example displays 600-800, according to example embodiments. The displays 600-800 include example data and may be generated by the client electronic device 102 and ultimately presented to an operator of the mobile electronic device 102 (e.g., the member). However, other types of displays and modification to the displays 600-800 may additionally or alternatively be presented. In this regard, while a number of different types of user interface elements have been reflected above, other types of user interface elements may be used to perform the same or similar functionality.

The display 600 of FIG. 7, is an example of an instant messaging display that may be presented to the device operator of the mobile electronic device. As shown in the display 600, the device operator may receive a text message 602 (or other communication) through which the device operator is invited to request a refill of a prescription via mail order by texting a picture of a prescription label to a specified number. In some embodiments, the text message 602 may be sent by the mail order conversion notification module 304.

For example, in some embodiments, it may be determined that the device operator, as a member of a health care plan, may be subject to mandatory home delivery of some, or all, prescription drugs. In response to determining that the device operator is subject to mandatory home delivery of prescription drugs, the prescription transfer management device 106, or another device, may transmit the text message 602 inviting the device operator to refill a prescription via mail order. It will be appreciated that, depending upon circumstance, the language of the text message (or other invitation or notice) may vary.

In some embodiments, the text message 602 may be sent to the device operator in response to the prescription transfer management device 106 determining that a prescription drug prescribed for the device operator may be eligible for mail order delivery. As such, the prescription transfer management device, and/or another device, may send the text message 602 inviting the device operator to transfer a prescription to mail order delivery. In some embodiments, the prescription transfer management device 106 may transmit a request for pre-approval of the transfer to mail order delivery of refills to the prescribing care provider. In response to receiving an affirmation of pre-approval from the prescribing care provider, the prescription transfer management device 106 may send the text message 602. It will be appreciated that, depending upon the circumstance, the language of the text message (or other invitation) may vary.

As shown in FIG. 8, if the device operator chooses to accept the invitation to have his prescription refilled by way of mail order, the device operator may utilize a camera functionality of the mobile electronic device 102, which may be accessible via a display 700, to take a picture 702 of the retail pharmacy prescription label on a container of a prescription drug.

FIG. 9 depicts a display 800 that enables the device operator to compose and sent a text message. For example, in an implementation, after taking the digital picture 702 of the retail pharmacy prescription label, the device operator may use the mobile electronic device 102 to transmit the digital picture to the mail order pharmacy at the number included within the invitation to transfer refills of the prescription to mail order. By using the mobile electronic device to transmit the picture 702 of the retail pharmacy prescription label to the number indicated in the text message 602, the device operator may be considered to have accepted the offer to receive refills of the prescription by mail order.

While the preceding example has generally depicted an embodiment in which the device operator may take a digital picture of a retail pharmacy prescription label with the mobile electronic device 102, and use the mobile electronic device 102 to transmit the digital picture to the mail order pharmacy as a text message, other implementations may be equally utilized. For example, as discussed above, the electronic image of the retail pharmacy prescription label may be sent via email and/or using a device other than the mobile electronic device. Various other implementations will be appreciated.

Figure 10:
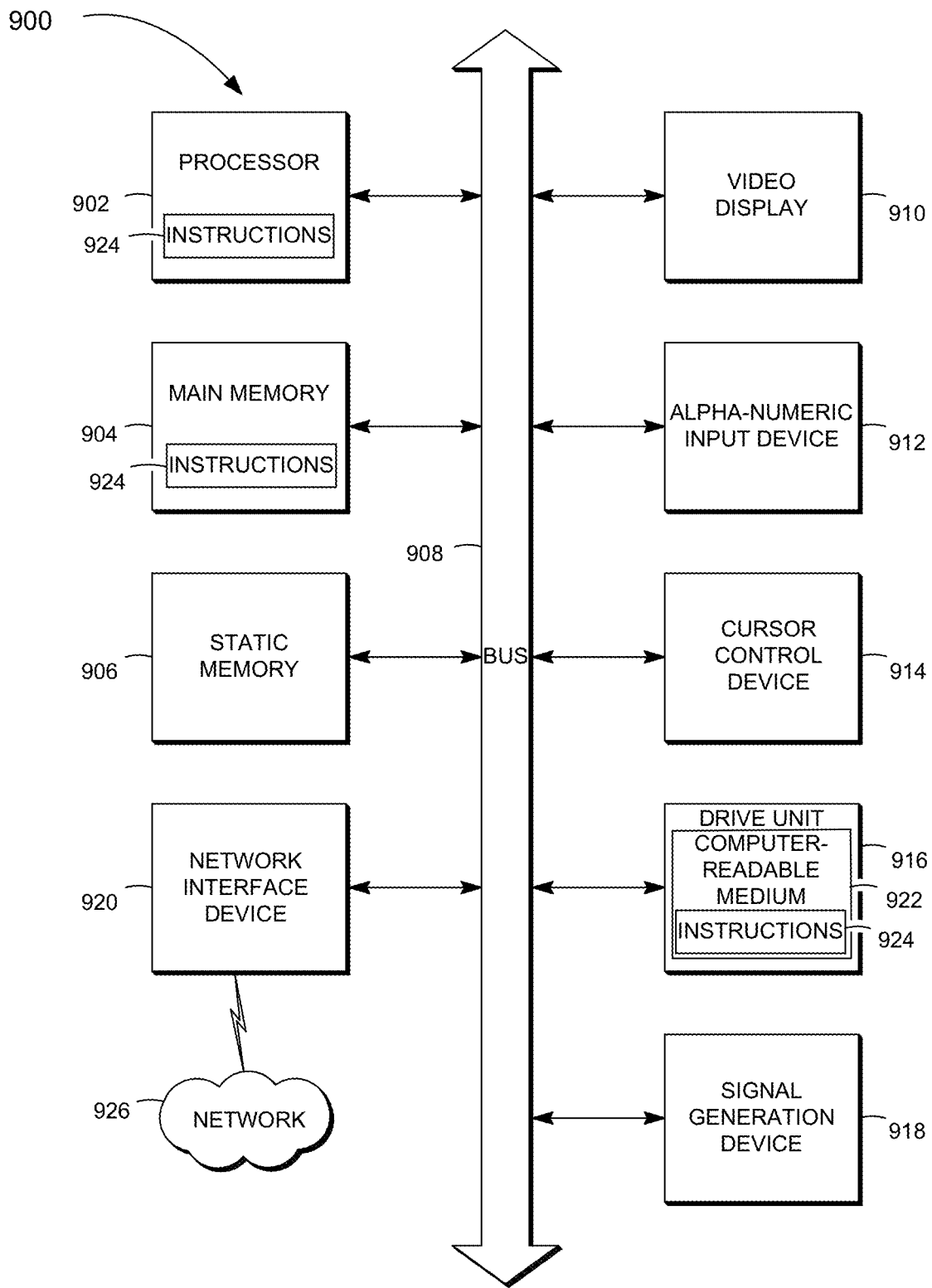
FIG. 10 is a block diagram of a machine in the example form of a computer system within which a set of instructions for causing the machine to perform any one or more of the methodologies discussed herein may be executed or stored.

FIG. 10 shows a block diagram of a machine in the example form of a computer system 900 within which a set of instructions may be executed causing the machine to perform any one or more of the methods, processes, operations, or methodologies discussed herein. The mobile electronic device 102, and/or the prescription transfer management device 106 may include the functionality of the one or more computer systems 900.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU) a graphics processing unit (GPU) or both), a main memory 904 and a static memory 906, which communicate with each other via a bus 908. The computer system 900 further includes a video display unit 910 (e.g., a liquid crystal display (LCD) or a cathode ray tube (CRT)). The computer system 900 also includes an alphanumeric input device 912 (e.g., a keyboard), a cursor control device 914 (e.g., a mouse), a drive unit 916, a signal generation device 918 (e.g., a speaker) and a network interface device 920.

The drive unit 916 includes a computer-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the computer system 900, the main memory 904 and the processor 902 also constituting computer-readable media.

The software 924 may further be transmitted or received over a network 926 via the network interface device 920.

While the computer-readable medium 922 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The inventive subject matter may be represented in a variety of different embodiments of which there are many possible permutations. In an example embodiment, an electronic image of a retail pharmacy prescription label is received, in which the image of the retail pharmacy prescription label includes a representation of a retail pharmacy prescription number associated with a prescription drug prescribed to a member. A retail pharmacy associated with the retail pharmacy prescription number is identified. A prescription associated with the retail pharmacy prescription number is identified based on identification of the retail pharmacy. A mail order delivery request to refill the prescription drug for the member at mail order is generated.

In another example embodiment a care provider associated with a prescription may be identified. A mail order delivery request may be transmitted to the care provider. A mail order conversion pre-approval may be received in response to transmission of the mail order delivery request. An electronic image of a retail pharmacy prescription label, including a representation of a retail pharmacy prescription number associated with a prescription drug prescribed to a member, may be received. A retail pharmacy associated with the retail pharmacy prescription number may be identified. A prescription associated with the retail pharmacy prescription number may be identified based on identification of the retail pharmacy. A mail order delivery conversion notification may be generated The terminology used herein is for the purpose of describing illustrative embodiments only and is not intended to be limiting of the invention. As used herein, the singular forms "a", "an" and "the" are intended to include the plural forms as well, unless the context clearly indicates otherwise. The term "based on" or using, as used herein, reflects an open-ended term that can reflect others elements beyond those explicitly recited. It will be further understood that the terms "comprises" and/or "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
receiving at one of a plurality of reception interfaces over a communication network in electronic communication with the one of a plurality of reception interfaces via a remote electronic device, by a processor, an electronic digital picture image of a retail pharmacy prescription label including a representation of a retail pharmacy prescription number associated with a prescription drug prescribed to a member and additional prescription information, the retail pharmacy prescription label being affixed to a prescription drug container or packaging provided to the member by a retail pharmacy, wherein the retail pharmacy fills the retail pharmacy prescription and is remote from the processor;

identifying an transmission source associated with the electronic digital picture image:

decoding, by the processor, the electronic digital picture image of the retail pharmacy prescription label including the retail pharmacy prescription number to identify the retail prescription for a patient with a multi-point congruence of information to meet a level of confidence in the prescription identification;

identifying, by the processor, the retail pharmacy associated with the retail pharmacy prescription number from the, decoded electronic image;

identifying, by the processor, the retail pharmacy prescription associated with the retail pharmacy prescription number based on identification of the retail pharmacy, the prescription being for the prescription drug;

determining, by the processor, whether the prescription drug is refill eligible using the retail pharmacy prescription number as decoded from the electronic image of the retail pharmacy prescription label;

identifying, by the processor, a care provider associated with the prescription;

generating, by the processor, a mail order delivery request to refill the prescription drug for the member at mail order based on receipt of the electronic image, identification of the prescription, and a determination that the prescription drug is refill eligible;

transmitting over the communication network the mail order delivery request to the care provider;

verifying that the transmission source is associated with the member while using the transmission source as one point of the multi-point congruence of information to identify the member and the prescription, wherein generating of the mail order request is further based on verification that the transmission source is associated with the member;

receiving over the communication network, by the processor, a mail order delivery authorization response from the care provider;

adjudicating, by the processor, the identified prescription; and scheduling, by the processor, a mail order delivery of a refill of the prescription drug from a mail order pharmacy to the member based upon receipt of the mail order delivery authorization response, adjudicating and the electronic image of the retail pharmacy prescription label.

2. The method of claim 1, further comprising:
transmitting a member mail order conversion notification to the remote electronic device,
wherein receipt of the electronic image over the communication network is in response to transmission of the member mail order conversion notification.

3. The method of claim 1, wherein determining whether the prescription drug is refill eligible comprises:
identifying a last fill date for the prescription; and
comparing the last fill date to a proposed mail date of the prescription drug.

4. The method of claim 1, wherein the electronic image includes a barcode representation of the retail pharmacy prescription number.

5. The method of claim 1, wherein the electronic image includes a plain text representation of the retail pharmacy prescription number, and identifying the prescription includes performing image recognition of the plain text representation of the retail pharmacy prescription number to generate the retail pharmacy prescription number.

6. The method of claim 1, wherein identifying the prescription includes determining member identification data, and querying a database including pharmacy claims data based upon the member identification data.

7. The method of claim 6, wherein the member identification data includes at least one of a member name, a member date of birth, and a member telephone number.

8. The method of claim 6, wherein determining member identification data includes performing image recognition of plain text information included in the electronic image of the retail pharmacy prescription label.

9. The method of claim 1, wherein generating the mail order delivery request includes pre-populating at least a portion of a mail order prescription.

10. The method of claim 1, wherein identification of the retail pharmacy comprises:
determining a retail pharmacy number included within the retail pharmacy prescription number; and
identifying the retail pharmacy associated with the retail pharmacy prescription number based on a determination of the retail pharmacy number.

11. The method of claim 1, wherein identification of the retail pharmacy comprises:
determining a retail pharmacy chain number included within the retail pharmacy prescription number; and
identifying the retail pharmacy associated with the retail pharmacy prescription number based on a determination of the retail pharmacy chain number.

12. The method of claim 1, wherein identification of the retail pharmacy comprises:
identifying retail pharmacy chain indicia included within the electronic image, the retail pharmacy chain indicia being separate from the retail pharmacy prescription number; and
identifying the retail pharmacy associated with the retail pharmacy prescription number based on identification of the retail pharmacy chain indicia.

13. The method of claim 1, further comprising:
identifying the prescription associated as having been adjudicated on behalf of the member;
identifying a care provider associated with the prescription;
transmitting a preapproval request to the care provider, the preapproval request seeking authorization to transfer the prescription from the retail pharmacy to the mail order pharmacy with member approval;
receiving a preapproval response confirming care provided authorization to transfer the prescription from the retail pharmacy to the mail order pharmacy with member approval, the preapproval response received prior to receipt of the electronic image of the retail pharmacy prescription label.

14. The method of claim 13, further comprising:
generating a member conversion notification based on receipt of the preapproval response,
wherein receipt of the electronic image of the retail pharmacy prescription label is in response to generation of the member conversion notification.

15. The method of claim 1, further comprising:
accessing benefit plan data associated with the member;
determining a number of times that a prescription drug refill of the prescription drug is permitted at retail in accordance with the plan data;

analyzing a plurality of prescription drug claims associated with the member to determine whether the member has met the number of allowable times for receiving the prescription drug refill of the prescription drug at retail; and transmitting a member mail order conversion notification based on as determination that the member has met the number of allowable times for receiving the prescription drug refill of the prescription drug at retail.

16. The method of claim 1, further comprising:

generating a pre-approval transfer authorization in response to identification of the care provider associated with the prescription, transmission of the mail order delivery request, and receipt of the mail order delivery authorization, wherein scheduling of the mail order delivery is based on generation of the pre-approval transfer authorization and receipt of the electronic image of the retail pharmacy prescription label; and filling the prescription at the mail order pharmacy.

17. The method of claim 1, wherein decoding the electronic digital picture image of the retail pharmacy prescription label includes decoding an image representation of a prescription number and a logo of the retail pharmacy to identify the retail pharmacy and the prescription number with the electronic digital picture image including a drug name sub-image, a patient name sub-image, and a dosage sub-image.

18. A non-transitory machine-readable medium comprising instructions, which, when executed by one or more processors, cause the one or more processors to perform the following operations:

receive at one of a plurality of reception interfaces over a network in electronic communication with the one of the plurality of reception interfaces, via a remote electronic device, an electronic digital picture image of a retail pharmacy prescription label including a representation of a retail pharmacy prescription number, as part of an image and not as an alphanumerical data, associated with a prescription drug prescribed to a member and additional prescription information, the retail pharmacy prescription label being affixed to a prescription drug container or packaging provided to the member by a retail pharmacy on fulfillment of the prescription drug;

identifying a transmission source associated with the electronic digital picture image;

verifying that the transmission source of the electronic digital picture image is associated with the member while using the transmission source to identify the prescription;

decode the electronic image of the retail pharmacy prescription label to obtain the retail pharmacy prescription number;

identify the retail pharmacy associated with the retail pharmacy prescription number;

identify a prescription associated with the retail pharmacy prescription number based on identification of the retail pharmacy, the prescription being for the prescription drug, wherein identifying includes identifying a prescription for a patient with a multi-point congruence of information to meet a level of confidence in the prescription identification;

determine whether the prescription drug is refill eligible using the retail pharmacy prescription number as decoded from the electronic image of the retail pharmacy prescription label;

identify a care provider associated with the prescription;

generate a mail order delivery request to refill the prescription drug for the member at mail order based on receipt of the electronic image, identification of the prescription, and a determination that the prescription drug is refill eligible, wherein generating of the mail order request is further based on verification that the transmission source is associated with the member;

transmit over the network the mail order delivery request to the care provider;

receive from the network a mail order delivery authorization response from the care provider;

adjudicate the identified prescription; and schedule a mail order delivery of a refill of the prescription drug from a mail order pharmacy to the member based upon receipt of the mail order delivery authorization response and the electronic image of the retail pharmacy prescription label.

19. The non-transitory machine-readable medium of claim 18, further comprising instruction for:

transmit a member mail order conversion notification, wherein receipt of the electronic image is in response to transmission of the member mail order conversion notification.

20. A system comprising:

an electronic device to capture an electronic digital picture image of a retail pharmacy prescription label including a digital picture representation of a retail pharmacy prescription number associated with a prescription drug prescribed to a member, wherein the digital picture representation of a retail pharmacy prescription number is in non-alphanumerical form;

a processor and a memory coupled to the processor, wherein the processor and the memory are remote from the electronic device and are in electrical communication with the electronic device over a communication network;

an image reception module deployed in the memory and executed by the processor to:

receive the electronic image of the retail pharmacy prescription label at one of a plurality of communication interface connected to the communication network, the electronic image including the representation of the retail pharmacy prescription number associated with the prescription drug prescribed to the member, the retail pharmacy prescription label being affixed to a prescription drug container or packaging provided to the member by a retail pharmacy on fulfillment of the prescription drug, identify an electronic source associated with the electronic image, and verify that at least one of the electronic source, a transmission source or both is associated with the member, wherein generation of a mail order request is further based on verification that the electronic source, the transmission source or both is associated with the member;

a pharmacy identification module deployed in the memory and executed by the processor to decode the electronic image of the retail pharmacy prescription label to obtain the retail pharmacy prescription number and identify the retail pharmacy associated with the retail pharmacy prescription number;

an adjudication module deployed in the memory and executed by the processor to adjudicate the identified prescription;

a prescription identification module deployed in the memory and executed by the processor to identify a prescription associated with the retail pharmacy prescription number based on identification of the retail pharmacy and to identify a care provider associated with the prescription, the prescription being for the prescription drug and to identify the prescription for a patient with a multi-point congruence of information to meet a level of confidence in the prescription identification;

an eligibility module deployed in the memory and executed by the processor to determine whether the prescription drug is refill eligible;

a request generation module deployed in the memory and executed by the processor to generate a mail order delivery request to refill the prescription drug for the member at mail order based on receipt of the electronic image, identification of the prescription, verification of the electronic source and a determination that the prescription drug is refill eligible;

a request transmission module deployed in the memory and executed by the processor to transmit the mail order delivery request to the care provider;

an approval module deployed in the memory and executed by the processor to receive a mail order delivery authorization response from the care provider; and the request generation module to schedule a mail order delivery of a refill of the prescription drug to the member based upon receipt of the mail order delivery authorization response and the electronic image of the retail pharmacy prescription label.

21. The system of claim 20, further comprising:

a conversion notification module deployed in the memory and executed by the processor to transmit a member mail order conversion notification, wherein receipt of the electronic image by the image reception module is in response to transmission of the member mail order conversion notification.

* * * * *